(12) United States Patent
Crook et al.

(10) Patent No.: US 6,737,430 B2
(45) Date of Patent: May 18, 2004

(54) MUTUAL PRODRUG OF AMLODIPINE AND ATORVASTATIN

(75) Inventors: Robert James Crook, Sandwich (GB); Alan John Pettman, Sandwich (GB)

(73) Assignee: Pfizer, Inc., New York, NY (US)

( * ) Notice: Subject to any disclaimer, the term of this patent is extended or adjusted under 35 U.S.C. 154(b) by 47 days.

(21) Appl. No.: 10/000,985

(22) Filed: Oct. 31, 2001

(65) Prior Publication Data

US 2002/0082282 A1 Jun. 27, 2002

Related U.S. Application Data

(60) Provisional application No. 60/255,025, filed on Dec. 12, 2000.

(30) Foreign Application Priority Data

Nov. 9, 2000 (GB) .............................................. 0027410

(51) Int. Cl.$^7$ .................. A61K 31/4439; C07D 401/12
(52) U.S. Cl. ..................................... 514/343; 546/276.4
(58) Field of Search ........................ 514/343; 546/276.4

(56) References Cited

U.S. PATENT DOCUMENTS 6,262,092 B1 * 7/2001 Chang et al. ................ 514/356
6,486,182 B1 * 11/2002 Chang et al. ................ 514/343

FOREIGN PATENT DOCUMENTS

| EP | 0089167 | 9/1983 | ......... C07D/211/90 |
|----|---------|--------|---------------------|
| EP | 0244944 | 11/1987 | ......... C07D/211/90 |
| EP | 0247633 | 12/1987 | ......... C07D/405/06 |
| EP | 0409281 | 1/1991 | ....... C07D/207/327 |
| EP | 0751938 | 5/1998 | ......... C07D/211/90 |
| EP | 0951906 | 10/1999 | .......... A61K/31/44 |
| EP | 0754043 | 5/2000 | .......... A61K/31/44 |
| WO | WO9911259 | 3/1999 | .......... A61K/31/40 |
| WO | WO 9911259 | 3/1999 | .......... A61K/31/40 |
| WO | WO0073271 | 12/2000 | ......... C07D/207/40 |
| WO | WO0073298 | 12/2000 | ......... C07D/401/12 |

OTHER PUBLICATIONS

Arrowsmith et al., J. Med. Chem., 1986, 29, 1696.
Rigby et al., J. Cardiovasc. Pharmacol, 12(Supp. 6) S144.
Brown and Goldstein, New England Journal of Medicine, 1981, 305, No. 9, 515–517.
The Scandinavian Simvastatin Survival Study (4S), Lancet, 1994, 344, 1383–89.
Shepherd et al. New England Journal of Medicine, 1995, 333, 1301–07.
Wilson et al, American Journal of cardiology, 1987, 59(14), 91G–94G.
Kramsch et al., Journal of Human Hypertension, 1995, Supp. 1, 53–59.
Lichtlen et al., Lancet, 1990, 335, 1109–13.
Waters et al., Circulation, 1990, 82, 1940–53.
Jukema et al, Circulation, 1995, Supp. 1, 1–197.
Orekhov et al, Cardiovascular Drugs and Therapy, 1997, 11, 350.

* cited by examiner

Primary Examiner—Patricia L. Morris
(74) Attorney, Agent, or Firm—Peter C. Richardson; Gregg C. Benson; Lisa A. Samuels

(57) ABSTRACT

The present invention relates to a mutual prodrug of amlodipine and atorvastatin, pharmaceutically acceptable acid addition salts thereof, pharmaceutical compositions thereof and the use of said prodrug and its salts in the manufacture of medicaments for the treatment of atherosclerosis, angina pectoris, combined hypertension and hyperlipidaemia and the management of cardiac risk.

21 Claims, No Drawings

MUTUAL PRODRUG OF AMLODIPINE AND ATORVASTATIN

CROSS REFERENCE TO RELATED APPLICATIONS

This claim is filed claiming priority from now abandoned U.S. Provisional Application No. 60/255,025, filed Dec. 12, 2000 and United Kingdom Application 0027410.0 filed Nov. 9, 2000.

FIELD OF THE INVENTION

The present invention relates to a mutual prodrug of amlodipine and atorvastatin, pharmaceutically acceptable acid addition salts thereof, pharmaceutical compositions thereof and the use of said prodrug and its salts in the manufacture of medicaments for the treatment of atherosclerosis, angina pectoris, combined hypertension and hyperlipidaemia and the management of cardiac risk.

BACKGROUND OF THE INVENTION

The conversion of 3-hydroxy-3-methylglutaryl-coenzyme A (HMG-CoA) to mevalonate is an early and rate-limiting step in the cholesterol biosynthetic pathway. This step is catalyzed by the enzyme HMG-CoA reductase. Statins inhibit HMG-CoA reductase from catalyzing this conversion. As such, statins are collectively potent lipid-lowering agents.

Atorvastatin hemicalcium, disclosed in European Patent No. 0409281, is currently sold as Lipitor™ and has the formula

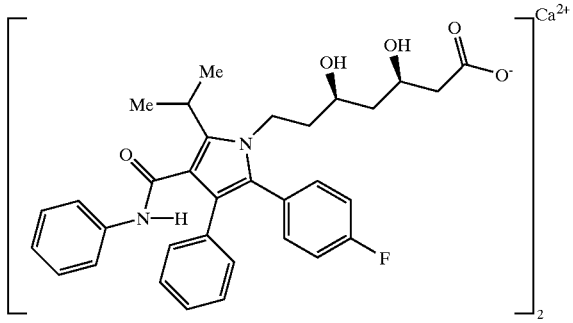

Atorvastatin hemicalcium is a selective, competitive inhibitor of HMG-CoA. As such, atorvastatin calcium is a potent lipid-lowering compound. The free carboxylic acid form of atorvastatin exists predominantly as the lactone of formula

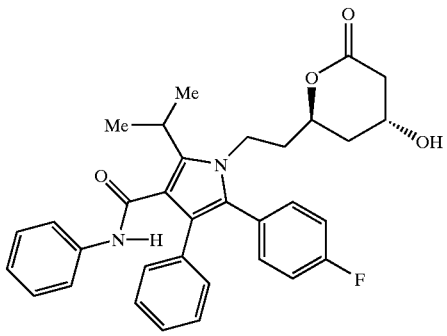

and is disclosed in European Patent No. 0247633.

Amlodipine and related dihydropyridine compounds are disclosed in European Patent No. 0089167 as potent antiischaemic and antihypertensive agents. European Patent No. 0244944 discloses amlodipine benzenesulphonate salt (also termed amlodipine besylate). Amlodipine and amlodipine besylate are potent and long-lasting calcium channel blockers. As such, amlodipine, amlodipine besylate and other pharmaceutically acceptable acid addition salts of amlodipine have utility as antiischaemic agents and as antihypertensive agents. Amlodipine and its pharmaceutically acceptable acid addition salts are also disclosed in European Patent No. 0951906 as having utility in the manufacture of a medicament for treating heart failure in a mammal. Amlodipine besylate is currently sold as Norvasc™.

Amlodipine has the formula

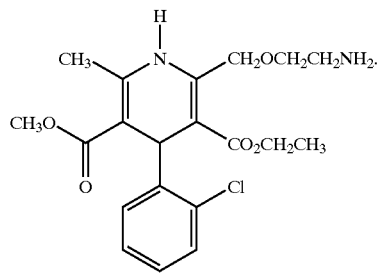

International Patent Application No. WO 99/11259 discloses therapeutic combinations comprising amlodipine and atorvastatin.

International Patent Application No. PCT/IB00/00590 describes the amlodipine salt of atorvastatin, that is, atorvastatin $CO_3^-$ amlodipine $NH_3^+$.

International Patent Application No. PCT/IB00/00313 describes a number of molecules wherein the atorvastatin and amlodipine moieties are linked through their respective carboxyl and amino groups by means of certain 'linkers', specifically —4-$OCH_2$-[2-keto-1,3-dioxolane]-5-$CH_2$— and —$OC(R^1R^2)OCO$— wherein $R^1$ and $R^2$ are independently selected from H and ($C_1$–$C_4$)alkyl.

It has now surprisingly been found that atorvastatin and amlodipine may be linked directly through their respective carboxyl and amino groups by means of a covalent amide bond.

Atherosclerosis is a condition characterized by irregularly distributed lipid deposits in the intima of arteries, including coronary, carotid and peripheral arteries. Atherosclerotic coronary heart disease (hereinafter termed "CHD") accounts for about 53% of all deaths attributable to a cardiovascular event. CHD accounts for nearly one-half (about $50–60 billion) of the total United States cardiovascular healthcare expenditures and about 6% of the overall national medical bill each year. Despite attempts to modify secondary risk factors, such as smoking, obesity and lack of exercise, and treatment of dyslipidaemia with dietary modification and drug therapy, CHD remains the most common cause of death in the United States.

High levels of blood cholesterol and blood lipids are conditions involved in the onset of atherosclerosis. It is well known that inhibitors of 3-hydroxy-3-methylglutaryl-coenzyme A reductase (HMG-CoA reductase) are effective in lowering the level of blood plasma cholesterol, especially low density lipoprotein cholesterol (LDL-C), in man (Brown and Goldstein, New England Journal of Medicine (1981), 305, No. 9, 515–517). It has now been established that lowering LDL-C levels affords protection from coronary heart disease (see, for example, The Scandinavian Simvastatin Survival Study Group: Randomised trial of cholesterol lowering in 4444 patients with coronary heart disease: the Scandinavian Simvastatin Survival Study (4S), Lancet (1994), 344, 1383–89; and Shepherd et al, Prevention of coronary heart disease with pravastatin in men with hypercholesterolemia, New England Journal of Medicine (1995), 333, 1301–07).

Angina pectoris is a severe constricting pain in the chest, often radiating from the precordium to the left shoulder and down the left arm. Often angina pectoris is due to ischaemia of the heart and is usually caused by coronary disease.

Currently the treatment of symptomatic angina pectoris varies significantly from country to country. In the United States, patients who present with symptomatic, stable angina pectoris are frequently treated by surgical procedures or PTCA. Patients who undergo PTCA or other surgical procedures designed to treat angina pectoris frequently experience complications, such as restenosis. This restenosis may be manifested either as a short-term proliferative response to angioplasty-induced trauma or as long-term progression of the atherosclerotic process in both graft vessels and angioplastied segments.

The symptomatic management of angina pectoris involves the use of a number of drugs, frequently as a combination of two or more of the following classes: beta-blockers, nitrates and calcium channel blockers. Most, if not all, of these patients require therapy with a lipid-lowering agent as well. The National Cholesterol Education Program (NCEP) recognizes patients with existing coronary artery disease as a special class requiring aggressive management of raised LDL-C.

Amlodipine helps to prevent myocardial ischaemia in patients with exertional angina pectoris by reducing Total Peripheral Resistance, or afterload, which reduces the rate pressure product and thus myocardial oxygen demand at any particular level of exercise. In patients with vasospastic angina pectoris, amlodipine has been demonstrated to block constriction and thus restore myocardial oxygen supply. Further, amlodipine has been shown to increase myocardial oxygen supply by dilating the coronary arteries.

Hypertension frequently coexists with hyperlipidaemia and both are considered to be major risk factors for developing cardiac disease ultimately resulting in adverse cardiac events. This clustering of risk factors is potentially due to a common mechanism. Further, patient compliance with the management of hypertension is generally better than patient compliance with hyperlipidaemia. It would therefore be advantageous for patients to have a single therapy which treats both of these conditions.

Coronary heart disease is a multifactorial disease in which the incidence and severity are affected by the lipid profile, the presence of diabetes and the sex of the subject. Incidence is also affected by smoking and left ventricular hypertrophy which is secondary to hypertension. To meaningfully reduce the risk of coronary heart disease, it is important to manage the entire risk spectrum. For example, hypertension intervention trials have failed to demonstrate full normalisation in cardiovascular mortality due to coronary heart disease. Treatment with cholesterol synthesis inhibitors in patients with and without coronary artery disease reduces the risk of cardiovascular morbidity and mortality.

The Framingham Heart Study, an ongoing prospective study of adult men and women, has shown that certain risk factors can be used to predict the development of coronary heart disease (see Wilson et al, Am. J. Cardiol. (1987), 59(14):91G–94G). These factors include age, gender, total cholesterol level, high density lipoprotein (HDL) level, systolic blood pressure, cigarette smoking, glucose intolerance and cardiac enlargement (left ventricular hypertrophy on electrocardiogram, echocardiogram, or enlarged heart on chest X-ray). Calculators and computers can easily be programmed using a multivariate logistic function that allows calculation of the conditional probability of cardiovascular events. These determinations, based on experience with 5,209 men and women participating in the Framingham study, estimate coronary artery disease risk over variable periods of follow-up. Modeled incidence rates range from less than 1% to greater than 80% over an arbitrarily selected six-year interval. However, these rates are typically less than 10% and rarely exceed 45% in men and 25% in women.

Kramsch et al, Journal of Human Hypertension (1995) Supp. 1, 53–59 discloses the use of calcium channel blockers, including amlodipine, to treat atherosclerosis. This reference further suggests that atherosclerosis can be treated with a combination of amlodipine and a lipid-lowering agent. Human trials have shown that calcium channel blockers have beneficial effects in the treatment of early atherosclerotic lesions (see, for example, Lichtlen et al, Retardation of angiographic progression of coronary artery disease by nifedipine, Lancet (1990), 335, 1109–13; and Waters et al, A controlled clinical trial to assess the effect of a calcium channel blocker on the progression of coronary atherosclerosis, Circulation (1990), 82, 1940–53). European Patent No. 0247633 discloses that certain statins, including atorvastatin, are hypolipidaemic agents and as such are useful in treating atherosclerosis. Jukema et al, Circulation (1995) Supp. 1, 1–197, discloses that there is evidence that calcium channel blockers act synergistically in combination with lipid-lowering agents, for example, HMG-CoA reductase inhibitors, specifically pravastatin. Orekhov et al, Cardiovascular Drugs and Therapy (1997), 11, 350 discloses the use of amlodipine in combination with lovastatin for the treatment of atherosclerosis.

SUMMARY OF THE INVENTION

The present invention is directed to a compound which is a mutual prodrug of amlodipine and atorvastatin having formula (I)

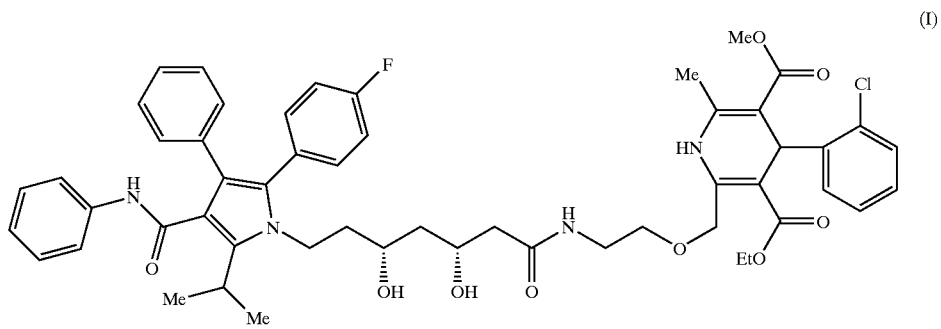

that is, 3-ethyl-5-methyl-2-{[2-({7-[3-anilinocarbonyl)-5-(4-fluorophenyl)-2-isopropyl-4-phenyl-1H-pyrrol-1-yl]-3,5-dihydroxyheptanoyl}amino)ethoxy]methyl}-4-(2-chlorophenyl)-6-methyl-1,4-dihydro-3,5-pyridine-dicarboxylate; and pharmaceutically acceptable salts thereof.

The invention is particularly directed to a compound of formula (I) wherein the carbon atom at the 4-position of the dihydropyridine ring in the amlodipine moiety has the (R) configuration and pharmaceutically acceptable salts thereof.

The invention is also particularly directed to a compound of formula (I) wherein the carbon atom at the 4-position of the dihydropyridine ring of the amlodipine moiety has the (S) configuration and pharmaceutically acceptable salts thereof.

The invention is also directed to the mutual prodrug of formula (I) or a pharmaceutically acceptable salt thereof for use as a medicine. Specifically, the invention is directed to the prodrug of formula (I) or a pharmaceutically acceptable salt thereof for use in the treatment of the conditions described herein by providing amlodipine and atorvastatin in vivo by hydrolytic cleavage of the amide bond.

The invention is also directed to the use of the mutual prodrug of formula (I) or a pharmaceutically acceptable salt thereof in the manufacture of a medicament for the treatment of the conditions described herein.

The invention is specifically directed to the use of the mutual prodrug of formula (I) or a pharmaceutically acceptable salt thereof in the manufacture of a medicament for the treatment of atherosclerosis. in particular, the invention is directed to those cases where said antiatherosclerotic effect is manifested by a slowing of the progression of atherosclerotic plaques, including wherein said atherosclerotic plaque formation is slowed in coronary arteries, carotid arteries, or in the peripheral arterial system. The invention is also particularly directed to those cases where said antiatherosclerotic effect is manifested by a regression of atherosclerotic plaques, including wherein said regression occurs in the coronary arteries, in the carotid arteries and/or in the peripheral arterial system.

The invention is specifically directed to the use of the mutual prodrug of formula (I) or a pharmaceutically acceptable salt thereof in the manufacture of a medicament for the treatment of angina pectoris.

The invention is specifically directed to the use of the mutual prodrug of formula (I) or a pharmaceutically acceptable salt thereof in the manufacture of a medicament for the treatment of combined hypertension and hyperlipidaemia.

The invention is specifically directed to the use of the mutual prodrug of formula (I) or a pharmaceutically accept-able salt thereof in the manufacture of a medicament for the management of cardiac risk.

The invention is also directed to pharmaceutical compositions obtained thereby which comprise a mutual prodrug of formula (I), that is, 3-ethyl-5-methyl-2-{[2-({7-[3-anilinocarbonyl)-5-(4-fluorophenyl)-2-isopropyl-4-phenyl-1H-pyrrol-1-yl]-3,5-dihydroxyheptanoyl}amino)ethoxy]methyl}-4-(2-chlorophenyl)-6-methyl-1,4-dihydro-3,5-pyridinedicarboxylate, or a pharmaceutically acceptable salt thereof, and a pharmaceutically acceptable excipient, diluent, or carrier. The invention is particularly directed to such compositions wherein the prodrug is the (R) or (S) enantiomer as hereinbefore defined.

The invention is also directed to the use of the mutual prodrug of formula (I) or a pharmaceutically acceptable salt thereof in the manufacture of a medicament combined with amlodipine or a pharmaceutically acceptable salt thereof, for example, amlodipine besylate, for the treatment of the conditions described herein.

The invention is specifically directed to the use of the mutual prodrug of formula (I) or a pharmaceutically acceptable salt thereof in the manufacture of a medicament combined with amlodipine or a pharmaceutically acceptable salt thereof, for example, amlodipine besylate, for the treatment of atherosclerosis.

The invention is specifically directed to the use of the mutual prodrug of formula (I) or a pharmaceutically acceptable salt thereof in the manufacture of a medicament combined with amlodipine or a pharmaceutically acceptable salt thereof, for example, amlodipine besylate, for the treatment of angina pectoris.

The invention is specifically directed to the use of the mutual prodrug of formula (I) or a pharmaceutically acceptable salt thereof in the manufacture of a medicament combined with amlodipine or a pharmaceutically acceptable salt thereof, for example, amlodipine besylate, for the treatment of combined hypertension and hyperlipidaemia.

The invention is specifically directed to the use of the mutual prodrug of formula (I) or a pharmaceutically acceptable salt thereof in the manufacture of a medicament combined with amlodipine or a pharmaceutically acceptable salt thereof, for example, amlodipine besylate, for the management of cardiac risk.

The invention is also directed to pharmaceutical compositions obtained thereby which comprise an amount of the mutual prodrug of formula (I) or a pharmaceutically acceptable salt thereof and an amount of amlodipine or a pharmaceutically acceptable salt thereof, for example, amlodipine besylate, and a pharmaceutically acceptable excipient, diluent, or carrier.

The invention is also directed to the use of the mutual prodrug of formula (I) or a pharmaceutically acceptable salt thereof in the manufacture of a medicament combined with atorvastatin or a pharmaceutically acceptable salt thereof, for example, atorvastatin hemicalcium, for the treatment of the conditions described herein.

The invention is specifically directed to the use of the mutual prodrug of formula (I) or a pharmaceutically acceptable salt thereof in the manufacture of a medicament combined with atorvastatin or a pharmaceutically acceptable salt thereof, for example, atorvastatin hemicalcium, for the treatment of atherosclerosis.

The invention is specifically directed to the use of the mutual prodrug of formula (I) or a pharmaceutically acceptable salt thereof in the manufacture of a medicament combined with atorvastatin or a pharmaceutically acceptable salt thereof, for example, atorvastatin hemicalcium, for the treatment of angina pectoris.

The invention is specifically directed to the use of the mutual prodrug of formula (I) or a pharmaceutically acceptable salt thereof in the manufacture of a medicament combined with atorvastatin or a pharmaceutically acceptable salt thereof, for example, atorvastatin hemicalcium, for the treatment of combined hypertension and hyperlipidaemia.

The invention is specifically directed to the use of the mutual prodrug of formula (I) or a pharmaceutically acceptable salt thereof in the manufacture of a medicament combined with atorvastatin or a pharmaceutically acceptable salt thereof, for example, atorvastatin hemicalcium, for the management of cardiac risk.

The invention is also directed to pharmaceutical compositions obtained thereby which comprise an amount of the mutual prodrug of formula (I) or a pharmaceutically acceptable salt thereof and an amount of atorvastatin or a pharmaceutically acceptable salt thereof, for example, atorvastatin hemicalcium, and a pharmaceutically acceptable excipient, diluent, or carrier.

DETAILED DESCRIPTION OF THE INVENTION

Amlodipine is a racemic compound due to the chiral carbon atom at the 4-position of the dihydropyridine ring. The (R) and (S) enantiomers may be prepared as described by Arrowsmith et al, J. Med. Chem. (1986), 29, 1696 and in European Patent No. 0751938. The calcium channel blocking activity of amlodipine is substantially confined to the (S) enantiomer and to the racemic mixture containing the (R) and (S) forms (see Rigby et al, J. Cardiovasc. Pharmacol., 12 (Supp. 6), S144). The (R) enantiomer has little or no calcium channel blocking activity, but is a potent inhibitor of smooth muscle cell migration. Thus the (R) enantiomer is useful in the treatment or prevention of atherosclerosis (see, for example, European Patent No. 0754043). Based on the above, a skilled person could choose to prepare an isomer of the mutual prodrug of formula (I) wherein the amlodipine portion is in the (R) configuration, the (S) configuration, or is a racemic mixture of the (R) and (S) configurations.

Where used herein and in the appendant claims, the term "cardiac risk" means the likelihood that a subject will suffer a future adverse cardiac event, such as myocardial infarction, cardiac arrest, cardiac failure, or cardiac ischaemia. Cardiac risk is calculated using the Framingham Risk Equation as described above. The term "cardiac risk management" means that the risk of future adverse cardiac events is substantially reduced.

The mutual prodrug of the invention may readily be prepared as set forth in the following description and in the Examples below. Specifically, to prepare the mutual prodrug of formula (I), equimolar amounts of amlodipine free base and atorvastatin free acid (predominantly in the form of the lactone) are refluxed together in a suitable solvent, typically ethanol, and the oil obtained after solvent removal purified by column chromatography to give the desired product.

Amlodipine may readily be prepared as described in European Patent No. 0089167. Amlodipine besylate, which is currently sold as Norvasc®, may be prepared as described in European Patent No. 0244944. Amlodipine and amlodipine besylate are potent and long-lasting calcium channel blockers.

The (R) and (S) enantiomers of amlodipine may be prepared as described by Arrowsmith et al, J. Med. Chem. (1986), 29, 1696 and in European Patent No. 0751938.

Atorvastatin may readily be prepared as described in European Patent No. 0247633. The hemicalcium salt of atorvastatin, which is currently sold as Lipitor®, may readily be prepared as described in European Patent No. 0409281.

The expression "pharmaceutically acceptable acid addition salts" is intended to define, but is not limited to, such salts as the hydrochloride, hydrobromide, sulphate, hydrogen sulphate, phosphate, hydrogen phosphate, dihydrogenphosphate, acetate, besylate, succinate, citrate, methanesulphonate (mesylate) and p-toluenesulfonate (tosylate) salts.

The acid addition salts of the instant prodrug of amlodipine and atorvastatin may readily be prepared by reacting the free base form thereof with the appropriate acid. When the salt is of a monobasic acid (for example, the hydrochloride, the hydrobromide, the p-toluenesulphonate, or the acetate), the hydrogen form of a dibasic acid (for example, the hydrogen sulphate, or the succinate), or the dihydrogen form of a tribasic acid (for example, the dihydrogen phosphate, or the citrate), at least one molar equivalent and usually a molar excess of the acid is employed. However, when such salts as the sulphate, the hemisuccinate, the hydrogen phosphate, or the phosphate are desired, the appropriate and exact chemical equivalents of acid are generally used. The free base and the acid are usually combined in a co-solvent from which the desired salt precipitates or can otherwise be isolated by solvent removal and/or the addition of a non-solvent.

In addition, the mutual prodrug of formula (I) and its pharmaceutically acceptable salts may occur as hydrates or solvates. Such hydrates and solvates are also within the scope of the present invention.

As indicated, the mutual prodrug, pharmaceutical compositions and uses of the invention are directed to the treatment of (a) atherosclerosis, (b) angina pectoris and (c) any condition characterised by the presence of both hypertension and hyperlipidaemia in mammals, particularly humans. Further, since these diseases and conditions are closely related to the development of cardiac disease and adverse cardiac conditions, these compounds, compositions and uses, by virtue of their action as antiatherosclerotics, antianginals, antihypertensives and antihyperlipidaemics, are useful in (d) the management of cardiac risk.

(a) Treatment of Atherosclerosis

The utility of the compounds and compositions of the present invention as medical agents in the treatment of atherosclerosis in mammals, for example, humans, is demonstrated by their activity in conventional assays and in the clinical protocol described herein.

The study is a prospective randomised evaluation of the effect of the mutual prodrug of formula (I) and its pharmaceutically acceptable salts on the progression/regression of coronary and carotid artery disease. The study is used to show that the prodrug of formula (I) and its pharmaceutically acceptable salts are effective in slowing or arresting the progression or causing regression of existing coronary artery disease (CAD) in subjects with established disease as evidenced by changes in coronary angiography or carotid ultrasound.

This study is an angiographic documentation of coronary artery disease carried out as a double-blind, placebo-controlled trial of a minimum of about 500 subjects and preferably of about 780 to about 1200 subjects. It is especially preferred to study about 1200 subjects in this study. Subjects are admitted into the study after satisfying certain entry criteria set forth below.

Entry criteria: Subjects accepted for entry into this trial must satisfy certain criteria. Thus, the subject must be an adult, either male or female, aged 18–80 years of age in whom coronary angiography is clinically indicated. Subjects will have angiographic presence of a significant focal lesion such as 30% to 50% on subsequent evaluation by quantitative coronary angiography (QCA) in a minimum of one segment (non-PTCA, non-bypassed or non-MI vessel) that is judged not likely to require intervention over the next 3 years. It is required that the segments undergoing analysis have not been interfered with. Since percutaneous transluminal cardiac angioplasty (PTCA) interferes with segments by the insertion of a balloon catheter, non-PTCA segments are required for analysis. It is also required that the segments to be analyzed have not suffered a thrombotic event, such as a myocardial infarct (MI). Thus, the requirement for non-MI vessels. Segments that will be analyzed include: left main, proximal, mid and distal left anterior descending, first and second diagonal branch, proximal and distal left circumflex, first or largest space obtuse marginal, proximal, mid and distal right coronary artery. Subjects will have an ejection fraction of greater than 30% determined by catheterization or radionuclide ventriculography or ECHO cardiogram at the time of the qualifying angiogram or within the previous three months of the acceptance of the qualifying angiogram provided no intervening event such as a thrombotic event or procedure such as PTCA has occurred.

Generally, due to the number of patients and the physical limitations of any one facility, the study is carried out at multiple sites. At entry into the study, subjects undergo quantitative coronary angiography as well as B-mode carotid artery ultrasonography and assessment of carotid arterial compliance at designated testing centers. This establishes baselines for each subject. Once admitted into the test, subjects are randomized to receive amlodipine besylate (10 mg) and placebo or atorvastatin hemicalcium (10 mg) and placebo or the mutual prodrug of formula (I) or a pharmaceutically acceptable salt thereof (about 5 mg to about 160 mg). All doses set forth in this protocol are per day doses. The amount of amlodipine besylate may be varied as required. Generally, a subject will begin taking 10 mg and the amount will be titrated down to as little as 5 mg as determined by the clinical physician.

The subjects are monitored for a 1- to 3-year period, three years generally being preferred. B-mode carotid ultrasound assessment of carotid artery atherosclerosis and compliance are performed at regular intervals throughout the study. Generally, 6-month intervals are suitable. Typically, this assessment is performed using B-mode ultrasound equipment. However, a person skilled in the art may use other methods of performing this assessment.

Coronary angiography is performed at the conclusion of the 1- to 3-year treatment period. The baseline and post-treatment angiograms and the intervening carotid artery B-mode ultrasonograms are evaluated for new lesions or progression of existing atherosclerotic lesions. Arterial compliance measurements are assessed for changes from baseline and over the 6-month evaluation periods.

The primary objective of this study is to show that the mutual prodrug of formula (I) and its pharmaceutically acceptable salts reduce the progression of atherosclerotic lesions as measured by quantitative coronary angiography (QCA) in subjects with clinical coronary artery disease. QCA measures the opening in the lumen of the arteries measured.

The primary endpoint of the study is the change in the average mean segment diameter of the coronary artery tree. Thus the diameter of an arterial segment is measured at various portions along the length of that segment. The average diameter of that segment is then determined. After the average segment diameter of many segments has been determined, the average of all segment averages is determined to arrive at the average mean segment diameter. The mean segment diameter of subjects taking the mutual prodrug of formula (I) or a pharmaceutically acceptable salt thereof will decline more slowly, will be halted completely, or there will be an increase in the mean segment diameter. These results represent slowed progression of atherosclerosis, halted progression of atherosclerosis and regression of atherosclerosis respectively.

The secondary objective of this study is to show that the mutual prodrug of formula (I) and its pharmaceutically acceptable salts reduce the rate of progression of atherosclerosis in the carotid arteries as measured by the slope of the maximum intimal-medial thickness measurements averaged over 12 separate wall segments (Mean Max) as a function of time. The intimal-medial thickness of subjects taking the prodrug of formula (I) or a pharmaceutically acceptable salt thereof will increase more slowly, will cease to increase, or will decrease. These results represent slowed progression of atherosclerosis, halted progression of atherosclerosis and regression of atherosclerosis respectively.

(b) Treatment of Angina Pectoris

The utility of the compounds and compositions of the present invention as medical agents in the treatment of angina pectoris in mammals, for example, humans, is demonstrated by their activity in conventional assays and in the clinical protocol described herein.

The study is a double blind, parallel arm, randomised study to show the effectiveness of a mutual prodrug of formula (I) and its pharmaceutically acceptable salts in the treatment of angina pectoris.

Entry criteria: Subjects are males or females between 18 and 80 years of age with a history of typical chest pain associated with one of the following objective evidences of cardiac ischaemia: (1) stress test segment elevation of about one millimeter or more from the ECG; (2) positive treadmill stress test; (3) new wall motion abnormality on ultrasound; or (4) coronary angiogram with a significant qualifying stenosis. Generally a stenosis of about 30–50% is considered to be significant.

Each subject is evaluated for about ten to thirty-two weeks. At least ten weeks are generally required to complete the study. Sufficient subjects are used in this screen to ensure that about 200 to 800 subjects and preferably about 400 subjects are evaluated to complete the study. Subjects are screened for compliance with the entry criteria, set forth above, during a 4-week run-in phase. After the screening criteria are met, subjects are washed out from their current anti-anginal medication and stabilized on a long-acting nitrate such as nitroglycerin, isosorbide-5-mononitrate, or isosorbide dinitrate. The term "washed out", when used in connection with this screen, means the withdrawal of current anti-anginal medication so that substantially all of said medication is eliminated from the body of the subject. A period of eight weeks is preferably allowed for both the wash out period and for the establishment of the subject on stable doses of said nitrate. Subjects having one or two attacks of angina per week while on stable doses of long-acting nitrate are generally permitted to skip the wash out phase. After subjects are stabilised on nitrates, the subjects enter the randomisation phase provided the subjects continue to have either one or two angina attacks per week. In the randomisation phase, the subjects are randomly placed into one of the four arms of the study set forth below. After completing the wash out phase, subjects in compliance with the entry criteria undergo 24-hour ambulatory electrocardiogram (ECG), such as Holter monitoring, exercise stress testing, such as a treadmill, and evaluation of myocardial perfusion using PET (photon emission tomography) scanning to establish a baseline for each subject. When conducting a stress test, the speed of the treadmill and the gradient of the treadmill can be controlled by a technician. The speed of the treadmill and the angle of the gradient are generally increased during the test. The time intervals between each speed and gradient increase are generally determined using a modified Bruce Protocol.

After the baseline investigations have been completed, subjects are initiated on one of the following four arms of the study: (1) placebo; (2) atorvastatin hemicalcium (about 2.5 mg to about 160 mg); (3) amlodipine besylate (about 2.5 mg to about 20 mg); or (4) the mutual prodrug of formula (I)

(about 5 mg to about 160 mg). The subjects are then monitored for two to twenty-four weeks. It will be recognized by a person skilled in the art that a pharmaceutically acceptable salt of the prodrug of formula (I) may be used in the fourth arm of the study; calculation of the dosage amount for these forms of the prodrug is easily accomplished by performing a simple ratio relative to the molecular weights of the species involved.

After the monitoring period has ended, subjects undergo the following investigations: (1) 24-hour ambulatory ECG, such as Holter monitoring; (2) exercise stress testing (for example, treadmill using said modified Bruce Protocol); and (3) evaluation of myocardial perfusion using PET scanning. Patients keep a diary of painful ischaemic events and nitroglycerine consumption. It is generally desirable to have an accurate record of the number of anginal attacks suffered by the patient during the duration of the test. Since a patient generally takes nitroglycerin to ease the pain of an anginal attack, the number of times that the patient administers nitroglycerine provides a reasonably accurate record of the number of anginal attacks.

To demonstrate the effectiveness of the compounds and compositions of the invention and to determine the dosage amounts of the mutual prodrug of formula (I), the person conducting the test will evaluate the subject using the tests described. Successful treatment will yield fewer instances of ischaemic events as detected by ECG, will allow the subject to exercise longer, at a higher intensity level, or without pain on the treadmill, or will yield better perfusion or fewer perfusion defects by photoemission tomography (PET).

(c) Treatment of Combined Hypertension and Hyperlipidaemia

The utility of the compounds and compositions of the present invention as medical agents in the treatment of hypertension and hyperlipidaemia in mammals, for example, humans, suffering from a combination of hypertension and hyperlipidaemia is demonstrated by their activity in conventional assays and in the clinical protocol described herein.

The study is a double blind, parallel arm, randomised study to show the effectiveness of the mutual prodrug of formula (I) and its pharmaceutically acceptable salts in controlling both hypertension and hyperlipidaemia in subjects who have mild, moderate, or severe hypertension and hyperlipidaemia.

Each subject is evaluated for 10 to 20 weeks, preferably for 14 weeks. Sufficient subjects are used in this screen to ensure that about 400 to 800 subjects are evaluated to complete the study.

Entry criteria: Subjects are male or female adults between 18 and 80 years of age having both hypertension and hyperlipidaemia. The presence of hyperlipidaemia is evidenced by evaluation of the low density lipoprotein (LDL) level of the subject relative to certain positive risk factors. If the subject has no coronary heart disease (CHD) and has less than two positive risk factors, then the subject is considered to have hyperlipidaemia if the LDL of the subject is greater than or equal to 190. If the subject has no CHD and has two or more positive risk factors, then the subject is considered to have hyperlipidaemia if the LDL of the subject is greater than or equal to 160. If the subject has CHD, then the subject is considered to have hyperlipidaemia if the LDL of the subject is greater than or equal to 130.

Positive risk factors include (1) male over 45, (2) female over 55 wherein said female is not undergoing hormone replacement therapy (HRT), (3) family history of premature cardiovascular disease, (4) the subject is a current smoker, (5) the subject has diabetes, (6) an HDL of less than 45, and (7) the subject has hypertension. An HDL of greater than 60 is considered a negative risk factor and will offset one of the above mentioned positive risk factors.

The presence of hypertension is evidenced by a sitting diastolic blood pressure (BP) of greater than 90 or sitting systolic BP of greater than 140. All blood pressures are generally determined as the average of three measurements taken five minutes apart.

Subjects are screened for compliance with the entry criteria set forth above. After all screening criteria are met, subjects are washed out from their current antihypertensive and lipid-lowering medication and are placed on the NCEP ATP II Step 1 diet. The NCEP ATP II (adult treatment panel, 2nd revision) Step 1 diet sets forth the amount of saturated and unsaturated fat which can be consumed as a proportion of the total caloric intake. The term "washed out", where used in connection with this protocol, means the withdrawal of current antihypertensive and lipid-lowering medication so that substantially all of said medication is eliminated from the body of the subject. Newly diagnosed subjects generally remain untreated until the test begins. These subjects are also placed on the NCEP Step 1 diet. After the 4-week wash out and diet stabilisation period, subjects undergo the following baseline investigations: (1) blood pressure and (2) fasting lipid screen. The fasting lipid screen determines baseline lipid levels in the fasting state of a subject. Generally, the subject abstains from food for twelve hours, at which time lipid levels are measured.

After the baseline investigations are performed, subjects are started on one of the following: (1) a fixed dose of amlodipine besylate, generally about 2.5 mg to about 10 mg; (2) a fixed dose of atorvastatin hemicalcium, generally about 10 mg to about 80 mg; or (3) the mutual prodrug of formula (I) (about 5 mg to about 160 mg). Subjects remain on these doses for a minimum of six weeks, generally for no more than eight weeks. It will be recognized by a skilled person that a pharmaceutically acceptable salt of the mutual prodrug of formula (I) may be used in the third arm of the study; calculation of the dosage amount for these forms of the prodrug is easily accomplished by performing a simple ratio relative to the molecular weights of the species involved. The subjects return to the testing center at the conclusion of the six to eight weeks so that the baseline evaluations can be repeated. The blood pressure of the subject at the conclusion of the study is compared with the blood pressure of the subject upon entry. The lipid screen measures the total cholesterol, LDL-cholesterol, HDL-cholesterol, triglycerides, apoB, VLDL (very low density lipoprotein) and other components of the lipid profile of the subject. Improvements in the values obtained after treatment relative to pretreatment values indicate the utility of the test compound.

(d) Management of Cardiac Risk

The utility of the compounds and compositions of the present invention as medical agents in the management of cardiac risk in mammals, for example, humans, at risk for an adverse cardiac event is demonstrated by their activity in conventional assays and in the clinical protocol described herein.

The study is a double blind, parallel arm, randomised study to show the effectiveness of the mutual prodrug of formula (I) and its pharmaceutically acceptable salts in reducing the overall calculated risk of future events in subjects who are at risk for having future cardiovascular events. This risk is calculated by using the Framingham Risk Equation. A subject is considered to be at risk of having a future cardiovascular event if that subject is more than one standard deviation above the mean as calculated by the Framingham Risk Equation. The study is used to evaluate the efficacy of the prodrug of formula (I) and its pharmaceutically acceptable salts in controlling cardiovascular risk by controlling both hypertension and hyperlipidaemia in patients who have both mild to moderate hypertension and hyperlipidaemia.

Each subject is evaluated for ten to twenty weeks, preferably for fourteen weeks. Sufficient subjects are recruited to ensure that about 400 to 800 subjects are evaluated to complete the study.

Entry criteria: Subjects included in the study are male or female adult subjects between 18 and 80 years of age with a baseline five-year risk which risk is above the median for said subject's age and sex, as defined by the Framingham Heart Study, which is an ongoing prospective study of adult men and women showing that certain risk factors can be used to predict the development of coronary heart disease. The age, sex, systolic and diastolic blood pressure, smoking habits, presence or absence of carbohydrate intolerance, presence or absence of left ventricular hypertrophy, serum cholesterol and high density lipoprotein (HDL) of more than one standard deviation above the norm for the Framingham Population are all evaluated in determining whether a patient is at risk for adverse cardiac event. The values for the risk factors are inserted into the Framingham Risk equation and calculated to determine whether a subject is at risk for a future cardiovascular event.

Subjects are screened for compliance with the entry criteria set forth above. After all screening criteria are met, patients are washed out from their current antihypertensive and lipid-lowering medication and any other medication which will impact the results of the screen. The patients are then placed on the NCEP ATP II Step 1 diet, as described in the hypertension and hyperlipidemia section above. Newly diagnosed subjects generally remain untreated until the test begins. These subjects are also placed on the NCEP ATP II Step 1 diet. After the 4-week wash out and diet stabilization period, subjects undergo the following baseline investigations: (1) blood pressure; (2) fasting; (3) lipid screen; (4) glucose tolerance test; (5) ECG; and (6) cardiac ultrasound. These tests are carried out using standard procedures well known to persons skilled in the art. The ECG and the cardiac ultrasound are generally used to measure the presence or absence of left ventricular hypertrophy.

After the baseline investigations are performed, patients will be started on one of the following: (1) a fixed dose of amlodipine besylate (about 2.5 mg to about 10 mg); (2) a fixed dose of atorvastatin hemicalcium (about 10 mg to about 80 mg); or (3) the mutual prodrug of formula (I) (about 5 mg to about 160 mg). It will be recognized by a skilled person that a pharmaceutically acceptable salt of the prodrug of formula (I) may be used in the third arm of the study; calculation of the dosage amount for these forms of the prodrug is easily accomplished by performing a simple ratio relative to the molecular weights of the species involved. Patients are kept on these doses and are asked to return in six to eight weeks so that the baseline evaluations can be repeated. At this time the new values are entered into the Framingham Risk equation to determine whether the subject has a lower, greater, or no change in the risk of future cardiovascular event.

The above assays demonstrating the effectiveness of the mutual prodrug of formula (I) and its pharmaceutically acceptable salts in the treatment of angina pectoris, atherosclerosis, combined hypertension and hyperlipidaemia and the management of cardiac risk, also provide a means whereby the activities of the compounds of the invention can be compared between themselves and with the activities of other known compounds. The results of these comparisons are useful for determining dosage levels in mammals, including humans, for the treatment of such diseases.

The mutual prodrug of formula (I) can be administered alone, but will generally be administered in admixture with a suitable pharmaceutically acceptable excipient, diluent, or carrier selected with regard to the intended route of administration and standard pharmaceutical practice.

For example, the mutual prodrug of formula (I) can be administered orally, buccally, or sublingually in the form of tablets, capsules, ovules, elixirs, solutions, or suspensions, which may contain flavouring or colouring agents, for immediate-, delayed-, modified-, sustained-, pulsed-, or controlled-release applications.

Such tablets may contain excipients, such as microcrystalline cellulose, lactose, sodium citrate, calcium carbonate, dibasic calcium phosphate, glycine and starch (preferably corn, potato, or tapioca starch), disintegrants, such as sodium starch glycollate, croscarmellose sodium and certain complex silicates, and granulation binders, such as polyvinylpyrrolidone, hydroxypropylmethylcellulose (HPMC), hydroxypropylcellulose (HPC), sucrose, gelatin and acacia. Additionally, lubricating agents, such as magnesium stearate, stearic acid, glyceryl behenate and talc, may be included.

GENERAL EXAMPLE

A formulation of the tablet could typically contain between about 2.5 mg and about 20 mg of active compound, whilst tablet fill weights may range from 50 mg to 1000 mg. An example of a formulation for a 10 mg tablet is illustrated below:

| Ingredient | % w/w |
| --- | --- |
| Free base or salt form | 10.000* |
| Lactose | 64.125 |
| Starch | 21.375 |
| Croscarmellose sodium | 3.000 |
| Magnesium stearate | 1.500 |

*Quantity adjusted in accordance with drug activity.

The tablets are manufactured by a standard process, for example, direct compression or a wet or dry granulation process. The tablet cores may be coated with appropriate overcoats.

Solid compositions of a similar type may also be employed as fillers in gelatin capsules. Preferred excipients for this purpose include lactose, starch, a cellulose, milk sugar, or high molecular weight polyethylene glycols. For aqueous suspensions and/or elixirs, the prodrug of formula (I) may be combined with various sweetening or flavouring agents, colouring matter or dyes, with emulsifying and/or suspending agents and with diluents, such as water, ethanol, propylene glycol and glycerin, or with combinations thereof.

The mutual prodrug of formula (I) can also be administered parenterally, for example, intravenously, intraarterially, intraperitoneally, intrathecally, intraventricularly, intraurethrally, intrasternally, intracranially, intramuscularly, or subcutaneously, or it may be administered by infusion techniques. For such parenteral administration, it is best used in the form of a sterile aqueous solution which may contain other substances, for example, enough salts or glucose to make the solution isotonic with blood. If necessary, the aqueous solution should be suitably buffered (preferably to a pH of from 3 to 9). The preparation of suitable parenteral formulations under sterile conditions is readily accomplished by standard pharmaceutical techniques well-known to those skilled in the art.

For oral and parenteral administration to human patients, the daily dosage level of the mutual prodrug of formula (I) will usually be from about 0.04 mg/kg to about 0.3 mg/kg (in single or divided doses).

Thus tablets or capsules of the mutual prodrug of formula (I) may contain from about 2.5 mg to about 20 mg of active compound for administration singly or two or more at a time, as appropriate. The physician in any event will determine the actual dosage which will be most suitable for any individual patient and it will vary with the age, weight and response of the particular patient. The above dosages are exemplary of the average case. There can, of course, be individual instances where higher or lower dosage ranges are merited and such are within the scope of this invention. The skilled person will appreciate that, in the treatment of conditions such as those described herein, the prodrug of formula (I) may be taken as a single dose as needed or desired.

The mutual prodrug of formula (I) can also be administered intranasally or by inhalation and is conveniently delivered in the form of a dry powder inhaler or an aerosol spray presentation from a pressurised container, pump, spray, atomiser, or nebuliser, with or without the use of a suitable propellant, for example, dichlorodifluoromethane, trichlorofluoromethane, dichlorotetrafluoroethane, a hydrofluoroalkane, such as 1,1,1,2-tetrafluoroethane (HFA 134A [trade mark]) or 1,1,1,2,3,3,3-heptafluoropropane (HFA 227EA [trade mark]), carbon dioxide, or other suitable gas. In the case of a pressurised aerosol, the dosage unit may be determined by providing a valve to deliver a metered amount. The pressurised container, pump, spray, atomiser, or nebuliser may contain a solution or suspension of the active compound, for example, using a mixture of ethanol and the propellant as the solvent, which may additionally contain a lubricant, for example, sorbitan trioleate. Capsules and cartridges (made, for example, from gelatin) for use in an inhaler or insufflator may be formulated to contain a powder mix of the prodrug of formula (I) and a suitable powder base, such as lactose or starch.

Aerosol or dry powder formulations are preferably arranged so that each metered dose or "puff" contains from 2 mg to 10 mg of the mutual prodrug of formula (I) for delivery to the patient. The overall daily dose with an aerosol will be in the range of from about 2.5 mg to about 20 mg which may be administered in a single dose or, more usually, in divided doses throughout the day.

Alternatively, the mutual prodrug of formula (I) can be administered in the form of a suppository or pessary, or it may be applied topically in the form of a gel, hydrogel, lotion, solution, cream, ointment, or dusting powder. The prodrug of formula (I) may also be dermally or transdermally administered, for example, by the use of a skin patch. It may also be administered by the pulmonary, rectal, or ocular routes. For ophthalmic use, the prodrug of formula (I) can be formulated as a micronised suspension in isotonic, pH-adjusted, sterile saline or, preferably, as a solution in isotonic, pH-adjusted, sterile saline, optionally in combination with a preservative, such as a benzylalkonium chloride. Alternatively, it may be formulated in an ointment, such as petrolatum.

For topical application to the skin, the mutual prodrug of formula (I) can be formulated as a suitable ointment containing the active compound suspended or dissolved in, for example, a mixture with one or more of the following: mineral oil, liquid petrolatum, white petrolatum, propylene glycol, polyoxyethylene polyoxypropylene compound, emulsifying wax and water. Alternatively, it can be formulated as a suitable lotion or cream suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyldodecanol, benzyl alcohol and water.

The mutual prodrug of formula (I) may also be used in combination with a cyclodextrin. Cyclodextrins are known to form inclusion and non-inclusion complexes with drug molecules. Formation of a drug-cyclodextrin complex may modify the solubility, dissolution rate, bioavailability and/or stability of a drug molecule. Drug-cyclodextrin complexes are generally useful for most dosage forms and administration routes. As an alternative to direct complexation with the drug, the cyclodextrin may be used as an auxiliary additive, for example, as a carrier, diluent, or solubiliser. Alpha-, beta- and gamma-cyclodextrins are most commonly used and suitable examples are described in International Patent Applications WO-A-91/11172, WO-A-94/02518 and WO-A-98/55148.

It will be appreciated that all references herein to treatment include curative, palliative and prophylactic treatments.

The following Examples illustrate the preparation of compounds in accordance with the invention:

Example 1

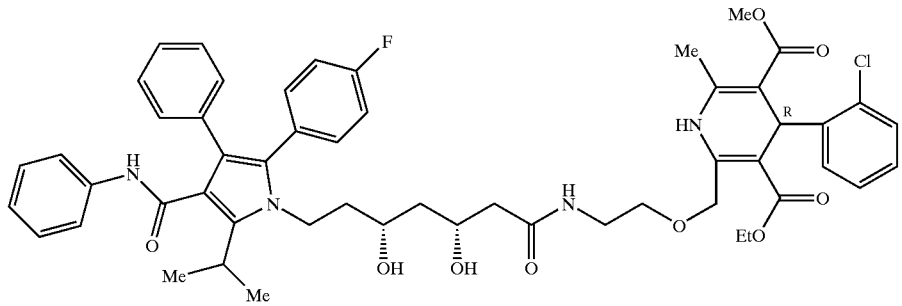

(R)-3-ethyl-5-methyl-2-{[2-({7-[3-anilinocarbonyl)-5-(4-fluorophenyl)-2-isopropyl-4-phenyl-1H-pyrrol-1-yl]-3,5-dihydroxyheptanoyl}amino)ethoxy]methyl}4-(2-chlorophenyl)-6-methyl-1,4-dihydro-3,5-pyridinedicarboxylate A solution of R(−)-amlodipine (840 mg, 2 mmol) and atorvastatin free acid (predominantly as the lactone) (1 g, 1.8 mmol) in ethanol (30 ml) was refluxed for 18 hours. The solvent was then evaporated in vacuo and the resulting oil purified by column chromatography using a standard silica column and eluting with 100% dichloromethane changing to 95%/5% dichloromethane/methanol. The desired product was obtained as a white foam (1.35 g, 76%). NMR (DMSO) d: 1.16–1.19 (t, 3H), 1.38–1.48 (m, 2H), 1.42–1.46 (d, 6H), 1.60–1.68 (m, 2H), 2.23–2.37 (d, 2H), 2.36 (s, 3H), 3.25–3.32 (m, 1H), 3.32–3.36 (m, 2H), 3.52–3.56 (m, 2H), 3.58–3.65 (m, 1H), 3.80–3.98 (m, 2H), 3.91–3.93 (m, 1H), 3.56 (s, 3H), 4.00–4.02 (m, 2H), 4.59–4.69 (d, 2H), 4.65 (s, 1H), 4.77 (s, 1H), 5.36 (s, 1H), 7.02–7.05 (m, 1H), 7.07–7.14 (m, 5H), 7.15–7.18 (m, 1H), 7.22–7.25 (m, 2H), 7.25–7.28 (m, 1H), 7.29–7.32 (m, 2H), 7.26–7.3 (m, 2H), 7.3–7.32 (m, 1H), 7.37–7.39 (m, 1H), 7.54–7.58 (d, 2H), 7.97 (t, 1H), 8.47 (s, 1H), 9.76 (s, 1H). MS (ESI): m/z [MNa$^+$] 971.5 Na$^+$ requires 971.5.

(S)-3-ethyl-5-methyl-2-{[2-({7-[3-anilinocarbonyl)-5-(4-fluorophenyl)-2-isopropyl-4-phenyl-1H-pyrrol-1-yl]-3,5-dihydroxyheptanoyl}amino)ethoxy]methyl}-4-(2-chlorophenyl)-6-methyl-1,4-dihydro-3,5-pyridinedicarboxylate A solution of S(+)-amlodipine (840 mg, 2 mmol) and atorvastatin free acid (predominantly as the lactone) (1 g, 1.8 mmol) in ethanol (30 ml) was refluxed for 18 hours. The solvent was then evaporated in vacuo and the resulting oil purified by column chromatography using a standard silica column and eluting with 100% dichloromethane changing to 95%/15% dichloromethane/methanol. The desired product was obtained as a white foam (1.14 g, 64%). NMR (DMSO) d: 1.16–1.19 (t, 3H), 1.38–1.48 (m, 2H), 1.42–1.46 (d, 6H), 1.60–1.68 (m, 2H), 2.23–2.37 (d, 2H), 2.36 (s, 3H), 3.25–3.32 (m, 1H), 3.32–3.36 (m, 2H), 3.52–3.56 (m, 2H), 3.58–3.65 (m, 1H), 3.80–3.98 (m, 2H), 3.91–3.93 (m, 1H), 3.56 (s, 3H), 4.00–4.02 (m, 2H), 4.59–4.69 (d, 2H), 4.65 (s, 1H), 4.77 (s, 1H), 5.36 (s, 1H), 7.02–7.05 (m, 1H), 7.07–7.14 (m, 5H), 7.15–7.18 (m, 1H), 7.22–7.25 (m, 2H), 7.25–7.28 (m, 1H), 7.29–7.32 (m, 2H), 7.26–7.3 (m, 2H), 7.3–7.32 (m, 1H), 7.37–7.39 (m, 1H), 7.54–7.58 (d, 2H), 7.97 (t, 1H), 8.47 (s, 1H), 9.76 (s, 1H). MS (ESI): m/z [MNa$^+$] 971.4 Na$^+$ requires 971.5.

Example 2

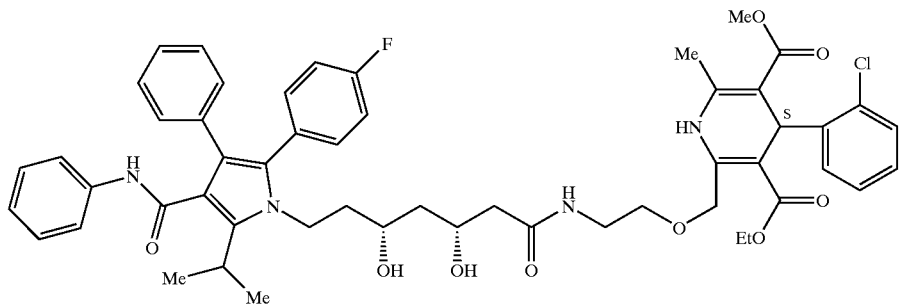

What is claimed is:

1. A compound of the formula (I),

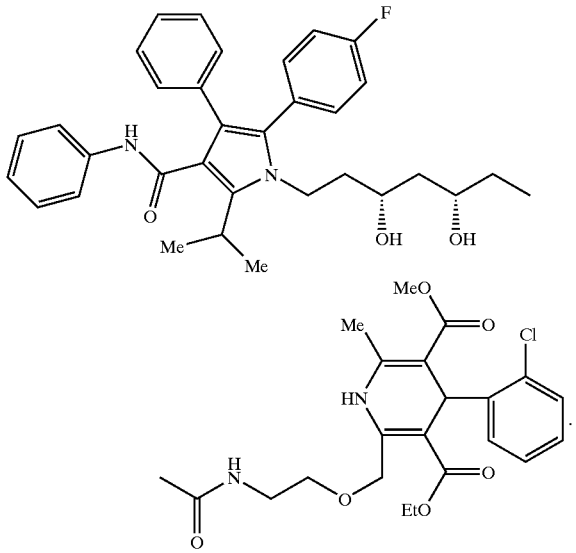

or a pharmaceutically acceptable salt thereof.

2. A compound of claim 1 which is (R)-3-ethyl-5-methyl-2-{[2-({7-[3-anilinocarbonyl)-5-(4-fluorophenyl)-2-isopropyl-4-phenyl-1H-pyrrol-1-yl]-3,5-dihydroxy-heptanoyl}amino)ethoxy]methyl}-4-(2-chlorophenyl)-6-methyl-1,4-dihydro-3,5-pyridinedicarboxylate, or a pharmaceutically acceptable salt thereof.

3. A compound of claim 1 which is (S)-3-ethyl-5-methyl-2-{[2-({7-[3-anilinocarbonyl)-5-(4-fluorophenyl)-2-isopropyl-4-phenyl-1H-pyrrol-1-yl]-3,5--dihydroxy-heptanoyl}amino)ethoxy]methyl}-4-(2-chlorophenyl)-6-methyl-1,4-dihydro-3,5-pyridinedicarboxylate, or a pharmaceutically acceptable salt thereof.

4. A pharmaceutical composition comprising a compound of claim 1 or a pharmaceutically acceptable salt thereof and a pharmaceutically acceptable excipient, diluent or carrier.

5. A pharmaceutical composition comprising a compound of claim 1 or a pharmaceutically acceptable salt thereof and a pharmaceutically acceptable excipient, diluent or carrier.

6. A pharmaceutical composition comprising a compound of claim 3 or a pharmaceutically acceptable salt thereof and a pharmaceutically acceptable excipient, diluent or carrier.

7. A method of treating atherosclerosis in a mammal comprising administering to said mammal an effective amount of a compound of claim 1, a pharmaceutically acceptable salt thereof or a pharmaceutical composition comprising said compound or said salt.

8. A method of beating atherosclerosis in a mammal comprising administering to said mammal an effective amount of a compound of claim 2, a pharmaceutically acceptable salt thereof or a pharmaceutical composition comprising said compound or said salt.

9. A method of beating atherosclerosis in a mammal comprising administering to said mammal an effective amount of a compound of claim 3, a pharmaceutically acceptable salt thereof or a pharmaceutical composition comprising said compound or said salt.

10. A method of treating angina pectoris in a mammal comprising administering to said mammal an effective amount of a compound of claim 1, a pharmaceutically acceptable salt thereof or a pharmaceutical composition comprising said compound or said salt.

11. A method of beating angina pectoris in a mammal comprising administering to said mammal an effective amount of a compound of claim 2, a pharmaceutically acceptable salt thereof or a pharmaceutical composition comprising said compound or said salt.

12. A method of treating angina pectoris in a mammal comprising administering to said mammal an effective amount of a compound of claim 3, a pharmaceutically acceptable salt thereof or a pharmaceutical composition comprising said compound or said salt.

13. A method of treating combined hypertension and hyperlipidemia in a mammal comprising administering to said mammal an effective amount of a compound of claim 1, a pharmaceutically acceptable salt thereof or a pharmaceutical composition comprising said compound or said salt.

14. A method of treating combined hypertension and hyperlipidemia in a mammal comprising administering to said mammal an effective amount of a compound of claim 2, a pharmaceutically acceptable salt thereof or a pharmaceutical composition comprising said compound or said salt.

15. A method of treating combined hypertension and hyperlipidemia in a mammal comprising administering to said mammal an effective amount of a compound of claim 3, a pharmaceutically acceptable salt thereof or a pharmaceutical composition comprising said compound or said salt.

16. A method of managing cardiac risk in a mammal comprising administering to said mammal an effective amount of a compound of claim 1, a pharmaceutically acceptable salt thereof or a pharmaceutical composition comprising said compound or said salt.

17. A method of managing cardiac risk in a mammal comprising administering to said mammal an effective amount of a compound of claim 2, a pharmaceutically acceptable salt thereof or a pharmaceutical composition comprising said compound or said salt.

18. A method of managing cardiac risk in a mammal comprising administering to said mammal an effective amount of a compound of claim 3, a pharmaceutically acceptable salt thereof or a pharmaceutical composition comprising said compound or said salt.

19. A process for the preparation of a compound of claim 1 comprising refluxing together amlodipine free base and atorvastatin free acid in a suitable solvent and isolating therefrom the compound of formula (I):

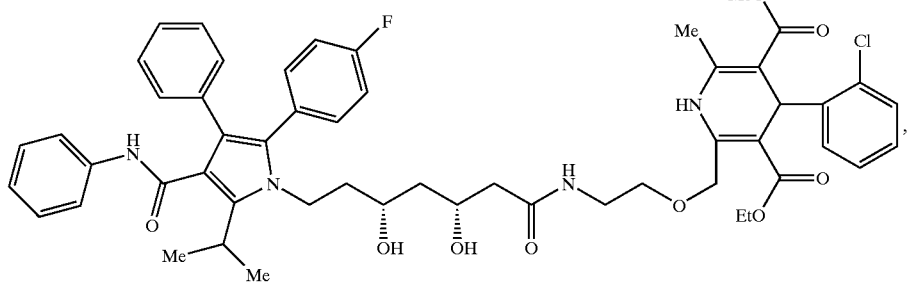
20. A process of claim 19 wherein said atorvastatin free acid is present predominatntly in the form of its tautomeric lactose.
21. A process of claim 20 wherein said solvent is ethanol.
* * * * *